US005759771A

United States Patent [19]
Tilanus

[11] Patent Number: 5,759,771
[45] Date of Patent: Jun. 2, 1998

[54] METHOD OF DETERMINING A GENOTYPE BY COMPARING THE NUCLEOTIDE SEQUENCE OF MEMBERS OF A GENE FAMILY AND KIT THEREFOR

[75] Inventor: Marcel G. J. Tilanus, Gruttoweide, Netherlands

[73] Assignee: The Perkin-Elmer Corporation, Foster City, Calif.

[21] Appl. No.: 39,137

[22] PCT Filed: Oct. 8, 1991

[86] PCT No.: PCT/US91/07308

§ 371 Date: Apr. 14, 1993

§ 102(e) Date: Apr. 14, 1993

[87] PCT Pub. No.: WO92/08117

PCT Pub. Date: May 14, 1993

[30] Foreign Application Priority Data

May 18, 1992 [NL] Netherlands ............... 9002259

[51] Int. Cl.$^6$ .................................. C12Q 1/68
[52] U.S. Cl. .................................. 435/6; 435/91.2
[58] Field of Search .................... 435/6, 91.2

[56] References Cited

U.S. PATENT DOCUMENTS

| 5,045,450 | 9/1991 | Thilly et al. | 435/6 |
| 5,066,377 | 11/1991 | Rosenbaum et al. | 204/182.8 |
| 5,110,920 | 5/1992 | Erlich | 536/24.31 |
| 5,192,659 | 3/1993 | Simons | 435/6 |
| 5,310,893 | 5/1994 | Erlich | 536/24.31 |

FOREIGN PATENT DOCUMENTS

| 237 362 A1 | 9/1987 | European Pat. Off. |
| 459 532 B1 | 12/1991 | European Pat. Off. |
| WO 89/11547 | 11/1989 | WIPO |
| WO 90/04040 | 4/1990 | WIPO |

OTHER PUBLICATIONS

Gyllensten et al. Proc. Natl. Acad. Sci, vol.85, Oct. 1988, 7652–56.

McBride L.J., et al., "Automated DNA Sequencing Methods Involving Polymerase Chain Reaction," *Clin. Chem.* 35(11):2196–2201 (1989).

Parham, P., et al., "Diversity and Diversification of HLA–A,B,C. Alleles," *J. Immun.* 142(11):3937–3950 (1989).

Scharf, S.J., et al., "Sequence Analysis of the HLA–DRβ and HLA–DQβ Loci from Three *Pemphigus vulgaris* Patients," *Human Immunology* 22:61–69 (1988).

Tilanus, M.G.J., et al., "A Family with an Apparent HLA DR Triplet: Evidence for Exchange of Functional HLA–DR Beta–Genes between Different Haplotypes," *Expl. Clin. Immunogenet* 6:162–168 (1989).

*Primary Examiner*—James Ketter
*Attorney, Agent, or Firm*—Vincent M. Powers; Gary R. Fabian

[57] ABSTRACT

A method is provided for determining a genotype by comparing the nucleotide sequence of members of a gene system which flank the polymorphous sections of a locus or loci of interest. In a general embodiment of the method, the nucleotide sequences chosen for comparison (i) contain one or two sequences that are completely conserved between the members of the gene family, where two or more members are selected from different sources, and (ii) the completely conserved sequences flank strongly conserved sections of genetic material. The completely conserved sequences are typically used to amplify, from different sources, the strongly conserved sections of genetic material. The resulting amplified nucleic acid sequences from the different sources are then compared to establish genotypes.

17 Claims, 5 Drawing Sheets

```
        32                                                      62
CGTTTCTTGTGGCAGCTTAAGTTTGAATGTCATTTCTTCAATGGGACGGAGCGGGTGCGG
ArgPheLeuTrpGlnLeuLysPheGluCysHisPhePheAsnGlyThrGluArgValArg
 R  F  L  W  Q  L  K  F  E  C  H  F  F  N  G  T  E  R  V  R
        92                                                     122
TTGCTGGAAAGATGCATCTATAACCAAGAGGAGTCCGTGCGCTTCGACAGCGACGTGGGG
LeuLeuGluArgCysIleTyrAsnGlnGluGluSerValArgPheAspSerAspValGly
 L  L  E  R  C  I  Y  N  Q  E  E  S  V  R  F  D  S  D  V  G
       152                                                     182
GAGTACCGGGCGGTGACGGAGCTGGGGCGGCCTGATGCCGAGTACTGGAACAGCCAGAAG
GluTyrArgAlaValThrGluLeuGlyArgProAspAlaGluTyrTrpAsnSerGlnLys
 E  Y  R  A  V  T  E  L  G  R  P  D  A  E  Y  W  N  S  Q  K
       212                                                     242
GACCTCCTGGAGCAGCGGCGGGCCGCGGTGGACACCTACTGCAGACACAACTACGGGGTT
AspLeuLeuGluGlnArgArgAlaAlaValAspThrTyrCysArgHisAsnTyrGlyVal
 D  L  L  E  Q  R  R  A  A  V  D  T  Y  C  R  H  N  Y  G  V

GGTGAGAGCTTCACAGTGCAGCGGCGAA
GlyGluSerPheThrValGlnArgArg
 G  E  S  F  T  V  Q  R  R
```

Fig. 2a

DR1
CGT TTC TTG TGG CAG CTT AAG TTT GAA TGT C
 R   F   L   W   Q   L   K   F   E   C

DR2·1
CGT TTC CTG TGG CAG CCT AAG AGG GAG TGT C
 R   F   L   W   Q   P   K   R   E   C

DR2·5
CGT TTC TTG CAG CAG GAT AAG TAT GAG TGT C
 R   F   L   Q   Q   D   K   Y   E   C

DRw6.w19
CGT TTC TTG GAG TAC TCT ACG TCT GAG TGT C
 R   F   L   E   Y   S   T   S   E   C

DRw6.52c
CGT TTC TTG GAG CTG CTT AAG AAG GAG TGT C
 R   F   L   E   L   L   K   K   E   C

Fig. 2b

DR1
TTG CTG GAA AGA TGC ATC TAT AAC CAA GAG
 L   L   E   R   C   I   Y   N   Q   E

DR2•1
TTC CTG GAC AGA TAC TTC TAT AAC CAG GAG
 F   L   D   R   Y   F   Y   N   Q   E

DR2•5
TTC CTG CAC AGA GAC ATC TAT AAC CAA GAG
 F   L   H   R   D   I   Y   N   Q   E

DRw6.w19
TTC CTG GAC AGA TAC TTC CAT AAC CAG GAG
 F   L   D   R   Y   F   H   N   Q   E

DRw6.52$^c$
TTC CTG GAC AGA TAC TTC CAT AAC CAG GAG
 F   L   D   R   Y   F   H   N   Q   E

Fig. 3a   Control DNA

```
              RFLWQLKFECHFFNGTERVRLLERCIYNQEESVRFD
DR1           ■■■■■                        ■■■■■■■
DR2■1         ----P-R-------------------F-D-YF---
DR2■5         ---Q-D-Y------------------F-H-D--DL
DRw6.w19      ---EYSTS------------------F-D-YFH-N
DRw6.52^C     ---EL--S------------------F-D-YFH-F
```

Fig. 3b   DNA family G

```
              -----                        -------
DR1           ■■■■■                        ■■■■■■■
DR1-like      --------------------------F-H-D--DL
DR2-like      ---E-A-C--I---------------F-H-D--DL
DRw6.w19      ---EYSTS------------------F-D-YFH-N
DRw6.52^C     ---EL--S------------------F-D-YFH-F
```

- = same amino acid as in DR1 at that position
■ = regions for ASO typing

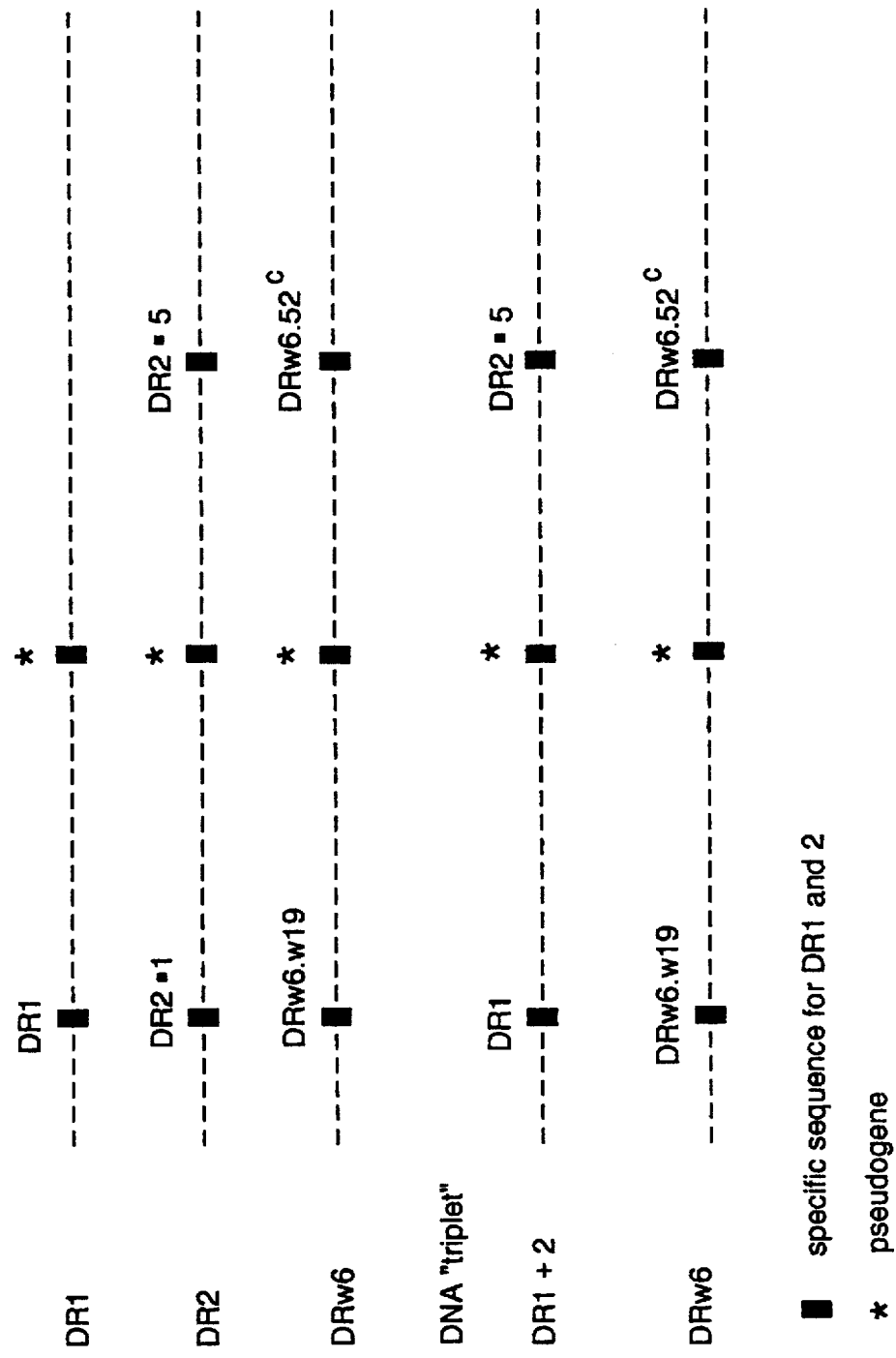

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DRB5 primer ( x i ) SEQUENCE DESCRIPTION: SEQ ID NO:1:

CCAGCACGTT TC                                                              1 2

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO (v i) ORIGINAL SOURCE:
    (C) INDIVIDUAL ISOLATE: DRB3 primer (x i) SEQUENCE DESCRIPTION: SEQ ID NO:2:

TTGTRTCTGC A      11

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: DQA5 primer (x i) SEQUENCE DESCRIPTION: SEQ ID NO:3:

CCATGAATTT GATGGAGA      18

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: DQA3 primer (x i) SEQUENCE DESCRIPTION: SEQ ID NO:4:

ATCGTTTAAT CA      12

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: DNA (i i i) HYPOTHETICAL: NO (i v) ANTI-SENSE: NO (v i) ORIGINAL SOURCE:
        (C) INDIVIDUAL ISOLATE: DQA3.1 primer (x i) SEQUENCE DESCRIPTION: SEQ ID NO:5:

TGTTCAAGTT RTGTTTT      17

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DQA3.2 primer (xi) SEQUENCE DESCRIPTION: SEQ ID NO:6:

ACAGCSATGT TTSTCAGTGC A                                                                 21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DXA3.2 primer (xi) SEQUENCE DESCRIPTION: SEQ ID NO:7:

ACAGCSATAT TTSTCAGTGC A                                                                 21

(2) INFORMATION FOR SEQ ID NO:8:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DXA3 primer (xi) SEQUENCE DESCRIPTION: SEQ ID NO:8:

TCTGCSGGTC AAAACT                                                                       16

(2) INFORMATION FOR SEQ ID NO:9:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (vi) ORIGINAL SOURCE:
        (C) INDIVIDUAL ISOLATE: DQB5 primer (xi) SEQUENCE DESCRIPTION: SEQ ID NO:9:

TGTGCTACTT CACCAA                                                                       16

( 2 ) INFORMATION FOR SEQ ID NO:10:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DQB3 primer ( x i ) SEQUENCE DESCRIPTION: SEQ ID NO:10:

GTAGTTGTGT CTGCA                                                                15

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DPB5 primer ( x i ) SEQUENCE DESCRIPTION: SEQ ID NO:11:

GCAGGAATGC TACGCGTTTA                                                           20

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DPB3 primer ( x i ) SEQUENCE DESCRIPTION: SEQ ID NO:12:

CCAGCTCGTA GTTGTGTCTG C                                                         21

( 2 ) INFORMATION FOR SEQ ID NO:13:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO 5,759,771

17

18

-continued ( i v ) ANTI-SENSE: NO ( v i ) ORIGINAL SOURCE:
    ( C ) INDIVIDUAL ISOLATE: DPB3SP primer ( x i ) SEQUENCE DESCRIPTION: SEQ ID NO:13:

TTGTAAAACG ACGGCCAGTC CAGCTCGTAG TTGTGTCTGC      40

( 2 ) INFORMATION FOR SEQ ID NO:14:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: APOE.F4 primer ( x i ) SEQUENCE DESCRIPTION: SEQ ID NO:14:

ACAGAATTCG CCCCGGCCTG GTACAC      26

( 2 ) INFORMATION FOR SEQ ID NO:15:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: APOE.F6 primer ( x i ) SEQUENCE DESCRIPTION: SEQ ID NO:15:

TAAGCTTGGC ACGGCTGTCC AAGGA      25

( 2 ) INFORMATION FOR SEQ ID NO:16:

( i ) SEQUENCE CHARACTERISTICS:
        ( A ) LENGTH: 268 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( C ) INDIVIDUAL ISOLATE: DR1 cDNA, Fig. 1

( i x ) FEATURE:
        ( A ) NAME/KEY: CDS
        ( B ) LOCATION: 1..267

( x i ) SEQUENCE DESCRIPTION: SEQ ID NO:16:

```
CGT  TTC  TTG  TGG  CAG  CTT  AAG  TTT  GAA  TGT  CAT  TTC  TTC  AAT  GGG  ACG      48
Arg  Phe  Leu  Trp  Gln  Leu  Lys  Phe  Glu  Cys  His  Phe  Phe  Asn  Gly  Thr
 1              5                        10                       15
```

-continued

| | | | | | | | | | | | | | | | | |
|---|---|---|---|---|---|---|---|---|---|---|---|---|---|---|---|---|
| GAG | CGG | GTG | CGG | TTG | CTG | GAA | AGA | TGC | ATC | TAT | AAC | CAA | GAG | GAG | TCC | 96 |
| Glu | Arg | Val | Arg | Leu | Leu | Glu | Arg | Cys | Ile | Tyr | Asn | Gln | Glu | Glu | Ser | |
| | | | 20 | | | | 25 | | | | | 30 | | | | |
| GTG | CGC | TTC | GAC | AGC | GAC | GTG | GGG | GAG | TAC | CGG | GCG | GTG | ACG | GAG | CTG | 144 |
| Val | Arg | Phe | Asp | Ser | Asp | Val | Gly | Glu | Tyr | Arg | Ala | Val | Thr | Glu | Leu | |
| | | 35 | | | | | 40 | | | | | 45 | | | | |
| GGG | CGG | CCT | GAT | GCC | GAG | TAC | TGG | AAA | CGG | CAG | AAG | GAC | CTC | CTG | GAG | 192 |
| Gly | Arg | Pro | Asp | Ala | Glu | Tyr | Trp | Lys | Arg | Gln | Lys | Asp | Leu | Leu | Glu | |
| | 50 | | | | | 55 | | | | | 60 | | | | | |
| CAG | AGG | CGG | GCC | GCG | GTG | GAC | ACC | TAC | TGC | AGA | CAC | AAC | TAC | GGG | GTT | 240 |
| Gln | Arg | Arg | Ala | Ala | Val | Asp | Thr | Tyr | Cys | Arg | His | Asn | Tyr | Gly | Val | |
| 65 | | | | 70 | | | | | 75 | | | | | 80 | | |
| GGT | GAG | AGC | TTC | ACA | GTG | CAG | CGG | CGA | A | | | | | | | 268 |
| Gly | Glu | Ser | Phe | Thr | Val | Gln | Arg | Arg | | | | | | | | |
| | | | | 85 | | | | | | | | | | | | |

( 2 ) INFORMATION FOR SEQ ID NO:17:

( i ) SEQUENCE CHARACTERISTICS:
        ( A ) LENGTH: 89 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

| | | | | | | | | | | | | | | | |
|---|---|---|---|---|---|---|---|---|---|---|---|---|---|---|---|
| Arg | Phe | Leu | Trp | Gln | Leu | Lys | Phe | Glu | Cys | His | Phe | Phe | Asn | Gly | Thr |
| 1 | | | | 5 | | | | | 10 | | | | | 15 | |
| Glu | Arg | Val | Arg | Leu | Leu | Glu | Arg | Cys | Ile | Tyr | Asn | Gln | Glu | Glu | Ser |
| | | | 20 | | | | 25 | | | | | 30 | | | |
| Val | Arg | Phe | Asp | Ser | Asp | Val | Gly | Glu | Tyr | Arg | Ala | Val | Thr | Glu | Leu |
| | | 35 | | | | | 40 | | | | | 45 | | | |
| Gly | Arg | Pro | Asp | Ala | Glu | Tyr | Trp | Lys | Arg | Gln | Lys | Asp | Leu | Leu | Glu |
| | 50 | | | | | 55 | | | | | 60 | | | | |
| Gln | Arg | Arg | Ala | Ala | Val | Asp | Thr | Tyr | Cys | Arg | His | Asn | Tyr | Gly | Val |
| 65 | | | | 70 | | | | | 75 | | | | | 80 | |
| Gly | Glu | Ser | Phe | Thr | Val | Gln | Arg | Arg | | | | | | | |
| | | | | 85 | | | | | | | | | | | |

( 2 ) INFORMATION FOR SEQ ID NO:18:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DR1 upstream fragment, Fig. 2A ( i x ) FEATURE:
        ( A ) NAME/KEY: CDS
        ( B ) LOCATION: 1..30

( x i ) SEQUENCE DESCRIPTION: SEQ ID NO:18:

| | | | | | | | | | | |
|---|---|---|---|---|---|---|---|---|---|---|
| CGT | TTC | TTG | TGG | CAG | CTT | AAG | TTT | GAA | TGT | C | 31 |
| Arg | Phe | Leu | Trp | Gln | Leu | Lys | Phe | Glu | Cys | | |
| 1 | | | | 5 | | | | | 10 | | |

( 2 ) INFORMATION FOR SEQ ID NO:19:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Arg Phe Leu Trp Gln Leu Lys Phe Glu Cys
 1               5                  10
```

( 2 ) INFORMATION FOR SEQ ID NO:20:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DR2*1 upstream fragment, Fig. 2A ( i x ) FEATURE:
        ( A ) NAME/KEY: CDS
        ( B ) LOCATION: 1..30

( x i ) SEQUENCE DESCRIPTION: SEQ ID NO:20:

```
CGT TTC CTG TGG CAG CCT AAG AGG GAG TGT C         31
Arg Phe Leu Trp Gln Pro Lys Arg Glu Cys
 1               5                  10
```

( 2 ) INFORMATION FOR SEQ ID NO:21:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

```
Arg Phe Leu Trp Gln Pro Lys Arg Glu Cys
 1               5                  10
```

( 2 ) INFORMATION FOR SEQ ID NO:22:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DR2*5 upstream fragment, Fig. 2A ( i x ) FEATURE:
        ( A ) NAME/KEY: CDS
        ( B ) LOCATION: 1..30

( x i ) SEQUENCE DESCRIPTION: SEQ ID NO:22:

```
CGT TTC TTG CAG CAG GAT AAG TAT GAG TGT C                                    31
Arg Phe Leu Gln Gln Asp Lys Tyr Glu Cys
 1               5                   10
```

( 2 ) INFORMATION FOR SEQ ID NO:23:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Arg Phe Leu Gln Gln Asp Lys Tyr Glu Cys
 1               5                   10
```

( 2 ) INFORMATION FOR SEQ ID NO:24:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DRw6.w19 upstream fragment, Fig. 2A ( i x ) FEATURE:
        ( A ) NAME/KEY: CDS
        ( B ) LOCATION: 1..30

( x i ) SEQUENCE DESCRIPTION: SEQ ID NO:24:

```
CGT TTC TTG GAG TAC TCT ACG TCT GAG TGT C                                    31
Arg Phe Leu Glu Tyr Ser Thr Ser Glu Cys
 1               5                   10
```

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Arg Phe Leu Glu Tyr Ser Thr Ser Glu Cys
 1               5                   10
```

( 2 ) INFORMATION FOR SEQ ID NO:26:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
        ( C ) INDIVIDUAL ISOLATE: DRw6.52c upstream fragment, Fig. 2A ( i x ) FEATURE:
  ( A ) NAME/KEY: CDS
  ( B ) LOCATION: 1..30

( x i ) SEQUENCE DESCRIPTION: SEQ ID NO:26:

| CGT | TTC | TTG | GAG | CTG | CTT | AAG | TCT | GAG | TGT | C | 31 |
| Arg | Phe | Leu | Glu | Leu | Leu | Lys | Ser | Glu | Cys | | |
| 1 | | | | 5 | | | | | 10 | | |

( 2 ) INFORMATION FOR SEQ ID NO:27:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:27:

Arg Phe Leu Glu Leu Leu Lys Ser Glu Cys
1               5                   10

( 2 ) INFORMATION FOR SEQ ID NO:28:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DR1 downstream fragment, Fig. 2b ( i x ) FEATURE:
    ( A ) NAME/KEY: CDS
    ( B ) LOCATION: 1..30

( x i ) SEQUENCE DESCRIPTION: SEQ ID NO:28:

| TTG | CTG | GAA | AGA | TGC | ATC | TAT | AAC | CAA | GAG | 30 |
| Leu | Leu | Glu | Arg | Cys | Ile | Tyr | Asn | Gln | Glu | |
| 1 | | | | 5 | | | | | 10 | |

( 2 ) INFORMATION FOR SEQ ID NO:29:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:29:

Leu Leu Glu Arg Cys Ile Tyr Asn Gln Glu
1               5                   10

( 2 ) INFORMATION FOR SEQ ID NO:30:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DR2*1 downstream fragment, Fig. 2b ( i x ) FEATURE:
    ( A ) NAME/KEY: CDS
    ( B ) LOCATION: 1..30

( x i ) SEQUENCE DESCRIPTION: SEQ ID NO:30:

```
TTC CTG GAC AGA TAC TTC TAT AAC CAG GAG      30
Phe Leu Asp Arg Tyr Phe Tyr Asn Gln Glu
 1           5                       10
```

( 2 ) INFORMATION FOR SEQ ID NO:31:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:31:

```
Phe Leu Asp Arg Tyr Phe Tyr Asn Gln Glu
 1           5                       10
```

( 2 ) INFORMATION FOR SEQ ID NO:32:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: DR2*5 downstream fragment, Fig. 2b ( i x ) FEATURE:
    ( A ) NAME/KEY: CDS
    ( B ) LOCATION: 1..30

( x i ) SEQUENCE DESCRIPTION: SEQ ID NO:32:

```
TTC CTG CAC AGA GAC ATC TAT AAC CAA GAG      30
Phe Leu His Arg Asp Ile Tyr Asn Gln Glu
 1           5                       10
```

( 2 ) INFORMATION FOR SEQ ID NO:33:

( i ) SEQUENCE CHARACTERISTICS:
    ( A ) LENGTH: 10 amino acids
    ( B ) TYPE: amino acid
    ( D ) TOPOLOGY: linear ( i i ) MOLECULE TYPE: protein ( x i ) SEQUENCE DESCRIPTION: SEQ ID NO:33:

```
Phe Leu His Arg Asp Ile Tyr Asn Gln Glu
 1           5                       10
```

( 2 ) INFORMATION FOR SEQ ID NO:34:

( i ) SEQUENCE CHARACTERISTICS:
    ( A ) LENGTH: 30 base pairs ( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DRw6.w19 downstream fragment, Fig. 2b ( i x ) FEATURE:
( A ) NAME/KEY: CDS
( B ) LOCATION: 1..30

( x i ) SEQUENCE DESCRIPTION: SEQ ID NO:34:

```
TTC CTG GAC AGA TAC TTC CAT AAC CAG GAG                           30
Phe Leu Asp Arg Tyr Phe His Asn Gln Glu
 1               5                  10
```

( 2 ) INFORMATION FOR SEQ ID NO:35:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( x i ) SEQUENCE DESCRIPTION: SEQ ID NO:35:

```
Phe Leu Asp Arg Tyr Phe His Asn Gln Glu
 1               5                  10
```

( 2 ) INFORMATION FOR SEQ ID NO:36:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
( C ) INDIVIDUAL ISOLATE: DRw6.52c downstream fragment, Fig. 2b ( i x ) FEATURE:
( A ) NAME/KEY: CDS
( B ) LOCATION: 1..30

( x i ) SEQUENCE DESCRIPTION: SEQ ID NO:36:

```
TTC CTG GAC AGA TAC TTC CAT AAC CAG GAG                           30
Phe Leu Asp Arg Tyr Phe His Asn Gln Glu
 1               5                  10
```

( 2 ) INFORMATION FOR SEQ ID NO:37:

( i ) SEQUENCE CHARACTERISTICS:
( A ) LENGTH: 10 amino acids
( B ) TYPE: amino acid
( D ) TOPOLOGY: linear ( i i ) MOLECULE TYPE: protein ( x i ) SEQUENCE DESCRIPTION: SEQ ID NO:37:

Phe Leu Asp Arg Tyr Phe His Asn Gln Glu
1               5                   10

( 2 ) INFORMATION FOR SEQ ID NO:38:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: DR1 protein fragment, Fig. 3a ( x i ) SEQUENCE DESCRIPTION: SEQ ID NO:38:

Arg Phe Leu Trp Gln Leu Lys Phe Glu Cys His Phe Phe Asn Gly Thr
1               5                   10                  15

Glu Arg Val Arg Leu Leu Glu Arg Cys Ile Tyr Asn Gln Glu Glu Ser
            20                  25                  30

Val Arg Phe Asp
            35

( 2 ) INFORMATION FOR SEQ ID NO:39:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: DR2*1 protein fragment, Fig. 3a ( x i ) SEQUENCE DESCRIPTION: SEQ ID NO:39:

Arg Phe Leu Trp Gln Pro Lys Arg Glu Cys His Phe Phe Asn Gly Thr
1               5                   10                  15

Glu Arg Val Arg Phe Leu Asp Arg Tyr Phe Tyr Asn Gln Glu Glu Ser
            20                  25                  30

Val Arg Phe Asp
            35

( 2 ) INFORMATION FOR SEQ ID NO:40:

( i ) SEQUENCE CHARACTERISTICS:
        ( A ) LENGTH: 36 amino acids
        ( B ) TYPE: amino acid
        ( C ) STRANDEDNESS: single
        ( D ) TOPOLOGY: unknown ( i i ) MOLECULE TYPE: protein ( i i i ) HYPOTHETICAL: NO ( i v ) ANTI-SENSE: NO ( v i ) ORIGINAL SOURCE:
        ( C ) INDIVIDUAL ISOLATE: DR2*5 protein fragment, Fig. 3a ( x i ) SEQUENCE DESCRIPTION: SEQ ID NO:40:

```
Arg Phe Leu Gln Gln Asp Lys Tyr Glu Cys His Phe Phe Asn Gly Thr
1               5                   10                  15

Glu Arg Val Arg Phe Leu His Arg Asp Ile Tyr Asn Gln Glu Glu Asp
            20                  25                  30

Leu Arg Phe Asp
        35
```

(2) INFORMATION FOR SEQ ID NO:41:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: DRw6.w19 protein fragment, Fig. 3a (xi) SEQUENCE DESCRIPTION: SEQ ID NO:41:

```
Arg Phe Leu Glu Tyr Ser Thr Ser Glu Cys His Phe Phe Asn Gly Thr
1               5                   10                  15

Glu Arg Val Arg Phe Leu Asp Arg Tyr Phe His Asn Gln Glu Glu Asn
            20                  25                  30

Val Arg Phe Asp
        35
```

(2) INFORMATION FOR SEQ ID NO:42:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: protein (iii) HYPOTHETICAL: NO (iv) ANTI-SENSE: NO (vi) ORIGINAL SOURCE:
        (C) INDIVIDUAL ISOLATE: DRw6.52c protein fragment, Fig. 3a (xi) SEQUENCE DESCRIPTION: SEQ ID NO:42:

```
Arg Phe Leu Glu Leu Leu Lys Ser Glu Cys His Phe Phe Asn Gly Thr
1               5                   10                  15

Glu Arg Val Arg Phe Leu Asp Arg Tyr Phe His Asn Gln Glu Glu Phe
            20                  25                  30

Val Arg Phe Asp
        35
```

(2) INFORMATION FOR SEQ ID NO:43:

(i) SEQUENCE CHARACTERISTICS:
        (A) LENGTH: 36 amino acids
        (B) TYPE: amino acid
        (C) STRANDEDNESS: single
        (D) TOPOLOGY: unknown (ii) MOLECULE TYPE: protein (iii) HYPOTHETICAL: NO (i v) ANTI-SENSE: NO (v i) ORIGINAL SOURCE:
  (C) INDIVIDUAL ISOLATE: DR1-like protein fragment, Fig. 3b (x i) SEQUENCE DESCRIPTION: SEQ ID NO:43:

```
Arg Phe Leu Trp Gln Leu Lys Phe Glu Cys His Phe Phe Asn Gly Thr
1               5                   10                      15

Glu Arg Val Arg Phe Leu His Arg Asp Ile Tyr Asn Gln Glu Glu Asp
            20                  25                  30

Leu Arg Phe Asp
        35
```

(2) INFORMATION FOR SEQ ID NO:44:

(i) SEQUENCE CHARACTERISTICS:
    (A) LENGTH: 36 amino acids
    (B) TYPE: amino acid
    (C) STRANDEDNESS: single
    (D) TOPOLOGY: unknown (i i) MOLECULE TYPE: protein (i i i) HYPOTHETICAL: NO (i v) ANTI-SENSE: NO (v i) ORIGINAL SOURCE:
    (C) INDIVIDUAL ISOLATE: DR2-like protein fragment, Fig. 3a (x i) SEQUENCE DESCRIPTION: SEQ ID NO:44:

```
Arg Phe Leu Glu Gln Ala Lys Cys Glu Cys His Ile Phe Asn Gly Thr
1               5                   10                      15

Glu Arg Val Arg Phe Leu His Arg Asp Ile Tyr Asn Gln Glu Glu Asp
            20                  25                  30

Leu Arg Phe Asp
        35
```

METHOD OF DETERMINING A GENOTYPE BY COMPARING THE NUCLEOTIDE SEQUENCE OF MEMBERS OF A GENE FAMILY AND KIT THEREFOR

This application is a continuation of PCT Application Ser. No. PCT/US91/07308 filed Oct. 8, 1991, which is based on Netherlands Application Serial No. 9002259 filed Oct. 17, 1990.

FIELD OF THE INVENTION

The invention relates to a method of determining a genotype by comparing members of a gene family, and also to a kit for tracing genetic variations in a gene family.

BACKGROUND

A gene system is composed of different loci which are in turn composed of one or more genes; these genes may contain variations, so-called different alleles, for each system. The immunoglobulin supergene family, which also includes, inter alia, the T-cell receptor, the immunoglobulin and the HLA (=human leukocyte antigen) gene systems, is characterised by the presence of a large variation (polymorphism). Each of the genes which form part of the gene systems is involved in the immune response in one way or another. Defects in the immune response, which are due to diverse variations in one or more of the gene systems already mentioned, may result in disease.

Genetic variation may thus be associated with diseases or disease symptoms. Identification of loci/alleles may therefore, for example, be of importance in determining the risk of a disease associated with HLA or in detecting variations in the gene system which result in a deviation, and variations for which the latter is not the case. Thus, the HLA-B27 antigen is/are found in 90% of all patients having rheumatoid spondylitis, and HLA-DR3 or HLA-DR4, or both, is/are found in 80% of patients afflicted with insulin-dependent diabetes. Anyone having HLA-B27 has 180 times as such change of getting rheumatodi spondylitis as a person without HLA-B27. Table I (taken from Biotechnologie, een nieuwe industriële revolutie (Biotechnology, A New Industrial Revolution), Antebi, E. and Fishlock, D., published by Natuur en Techniek, Maastricht/Brussels (1987) page 91) shows the most important diseases which are known to be associated with the HLA system. These locus and allele associations may render clinical practice a great service. They are sometimes used for diagnosis and sometimes in the treatment of certain diseases. They furthermore open up the possibility of prevention. It is possible to identify those which have the greatest risk of a particular disease. That is very important in those situations in which preventive or early treatment is possible and the development of the disease can be contained.

TABLE I

The most important diseases associated with the HLA system

| HLAs | Pathology | Relative risk* |
|---|---|---|
| A1 | Hodgkin's disease | 1.4 |
| A3 | Idiopathic haemochromatosis | 8.2 |
| B5 | Behcet's disease | 6.3 |
| B14, B47 | Congenital adrenal hyperplasia | 15.4 |
| B27 | Rheumatoid spondylitis | 87.4 |
| B35 | Subacute throiditis | 13.7 |
| Cw6 | Psoriasis | 13.3 |

TABLE I-continued

The most important diseases associated with the HLA system

| HLAs | Pathology | Relative risk* |
|---|---|---|
| DR2 | Multiple sclerosis | 4.1 |
| DR3 | Systemic lupus erythematosus | 5.8 |
| DR3 | Addison's disease | 6.3 |
| DR3 | Basedow's disease | 3.7 |
| DR3 | Myasthenia gravia | 2.5 |
| DR3 | Extramembranous glomerulopathy | 12.0 |
| DR3 and/or DR4 | Insulin-dependent diabetes | 6.4 |
| DR3 and/or DR7 | Coeliac disease | 4.8 |
| DR4 | Rheumatoid arthritis | 4.0 |
| DR4 | Pemphigus | 14.4 |
| DR5 | Biermer's anaemia | 5.4 |
| DR5 | Hashimoto's disease | 5.6 |
| DR5, DRw8 | Juvenile arthritis | 5.2 |

*The relative risk indicates the factor by which the risk of getting a disease is multiplied for people having the HLAs concerned. Individuals having group HLA-Cw6 have, for example, 13.3 times as much chance of getting psoriasis as people not having said antigen.

Genetic variation in the HLA system is furthermore of importance in view of the fact that acceptance in organ and tissue transplants is associated with the presence of the same HLA alleles in the white blood cells, while rejection is related to the presence of various HLA alleles in the white blood cells.

In man the HLA gene family covers a region of 1,500,000 base pairs. This region codes for many genes. Thus, this region contains, in addition to the genes of HLA class I and HLA class II, inter alia, genes of the complement system, 21-hydroxylase genes and genes which code for tumour necrosis factor.

The HLA class I region contains 3 "major"loci: HLA-A, HLA-B and HLA-C. The molecules for which said loci code are expressed in all nucleated cells. The molecules of class I are composed of a polymorphous α-chain having a molecular weight (MW) of 44,000 D and a constant chain, called $\beta_2$-microglobulin, having a MW of 12,000 D.

The HLA class II region contains the loci HLA-DR, HLA-DQ and HLA-DP. In addition to said loci, a number of genes are also described which do not belong to one of the abovementioned loci and are for the time being considered to be separate loci (for example, HLA-E; HLA-F; HLA-DN; HLA-DZ). The molecules of class II are composed of an α-chain (MW 34,000 D) and a β-chain (MW 29,000 D). The α-chain of HLA-DR is constant, i.e. no variants have yet been found. HLA-DR contains 3 β-genes, of which two genes code for a product and one gene is a pseuodgene which is therefore not expressed. Each of the β-chains can form dimeric molecules with the α-chain. The HLA-DQ locus contains four (two α- and two β-) genes, of which two are expressed, namely DQα and DQβ (termed DQA and DQB on the recommendation of the latest nomenclature committee). The molecule of the other genes (DXA and DXB) has not been found, although the structure of said genes indicates no characteristic pseudogenes. The HLA-DP locus contains four genes (two α and two β), of which two are expressed. Polymorphism has not yet been demonstrated for DPA, and only a few alleles of DPB have been described. The other two DP genes are pseudogenes.

A method of detecting specific nucleotide variations and genetic polymorphisms which are present in nucleic acids, and also a kit for carrying out said method are described in EP-A-237,362. Said method comprises amplifying nucleic acid sequences in which the presence of nucleotide variations, mutations and polymorphisms is assumed, followed by the detection thereof with allelespecific oligonucleotide sequences using a dot blot. In this process, allele-specific oligonucleotide sequences are used (see page 22 of the said patent application) which comprise at least the DNA sequence with the variation to be detected and have to be specific for the nucleotide variation to be detected. The kit therefore comprises many different primers which code for diverse known variations in the DNA sequence, to be investigated, of the gene system.

Immobilised sequence-specific oligonucleotide probes for the genetic analysis of amplified DNA are disclosed by the International Patent Application WO 89/11548 and by R. K. Saiki et al., Proc. Natl. Acad. Sci. USA. 86. 6230–6234 (1989).

A method of determining genotypes as regards the alleles in the HLA-DP loci by hybridising nucleic acid samples with a series of probes which are specific for various segments is disclosed by the International Patent Application WO 89/11547.

A method of distinguishing nucleotide sequences by hybridising amplified DNA with linkable probes is disclosed by the International Patent Application WO 90/01563.

These known methods have the following disadvantages:

a) It is only possible to trace known variations in the DNA sequence of a particular gene system, as a result of which any hitherto unknown variations in the gene system to be investigated cannot be discovered by said method.

b) It is necessary to include various oligonucleotides for every known variation in the kit and to use them in the method, with the result that, in complex gene systems which comprise many possible alleles (such as, for example, the HLA system), a different oligonucleotide has to be used for every possible allele and a different hybridisation has to be carried out, which is cumbersome, time-consuming and expensive.

HLA TYPING

Class I Serology

The HLA class I molecules are determined with the aid of antisera which are specific for individual alleles. In most cases, alloantisera are used because monoclonal antibodies against all the allele forms are not available. It is improbable that they will become available in the short term because the variation which characterises the polymorphism of the various alleles is localised in small region of the class I gene.

Class I protein

Protein-chemistry determination of the class I alleles is possible by means of immune precipitations with monoclonal antisera against constant sections of the molecules, followed by isoelectric focusing (IEF).

Class I DNA

Typing is possible to a limited extent by means of determinations of restriction fragment length polymorphism (RFLP) in which use is made of class I cDNA probes. Further refinement has yielded probes which are locus-specific, as a result of which clusters of alleles and some separate alleles can be detected. Typing of class I alleles by means of allele-specific oligohybridisations (ASO) is not considered possible as a result of the large number of different alleles and, consequently, the large number of oligos which is necessary. Routine typing at the DNA level is difficult to achieve by this method.

Class II serology is more difficult to carry out in practice, firstly because of the lack of well-defined antisera and secondly because of the elaborateness of the identification technique, viz. two-colour fluorescence.

Class II proteins can be characterised by means of IEF as a result of the availability of monoclonal antibodies, but the diversity of alleles in terms of variation and number makes the standard typing difficult, especially in heterozygous individuals.

Class II DNA

RFLP analyses can be used to identify DRA, DQA, DQB and DPB alleles. In this connection, some alleles are placed in a "supertypic group" because they cannot be distinguished individually, but stand out as a group of alleles having a specific RFLP pattern from the other alleles.

The technique of Southern blot analyses resulting in RFLP patterns is readily usable for typing class II. Viewed technically, this approach is not suitable for routing class II typing because of its elaborateness.

The development of ASO typing with synthetic oligonucleotides on amplified DNA by means of the polymerase chain reaction (PCR) has now made routine typing of DQA possible. Typing will have to be developed still further for DRB, DQB and DBP. A disadvantage of this method is that a large number of allele-specific oligos has to be used as the number of alleles of the locus concerned increases.

WORKSHOP

Every year the results of the HLA typing centres distributed around the world are examined at a workshop, sera being selected and defined as reference sera. The improvements in typing by means of protein-chemistry determinations. DNA/RFLP and DNA-ASO analysis is facilitating the standardisation of alleles determined with antisera.

As regards protein typing, the workshop determines which monoclonal antibodies have to be used and how the data have to be interpreted. For DNA-RFLP typing, the enzyme-probe combination is determined, in addition to a standardisation of DNA isolations and hybridisations.

DNA-ASO typing is offered as a package by Perkin-Elmer/Cetus Corporation (patented and marketed as a kit) and can now be used for DQA typing.

Attempts are being made to find a combination of the various methods which can be carried out uniformly by every typing centre throughout the world. In this connection, the reproducibility of the determinations in various typing centres, the uniformity of reagents (sera, probes, oligos) and the possibility of carrying out quality controls of the typing play an important role.

In the abovementioned cases, the approach to typing is based on the characterisation of the polymorphous sections of the molecules or genes of the loci.

SUMMARY OF THE INVENTION

It has now been found that use can advantageously be made of conserved sequences which flank the polymorphous system, to determine genetic variations.

The method according to the invention for determining a genotype by comparing the nucleotide sequence of members of a gene system is therefore characterised in that the nucleotide sequence of a locus or gene of a strongly conserved section is compared in which the polymorphism is localised the genetic material.

An important advantage of the method according to the invention is that deviations in a gene system, and especially deviations which are expressed, can be traced more easily and with greater certainty by means of it. More particularly, the advantages of the present method are:

New mutations can be detected directly and can then be investigated in more detail for functionality. This is in contrast to serological typing, in which at most a cross reaction with other sera but more often no reaction, is found. ASO typing characterises them as negative for that allele.

The method is independent of known polymorphisms compared with other determinations.

Owing to the simplicity of the system (high degree of reproducibility throughout the world), standardisation of typing will be simplified.

The method is independent of geographically determined internal variations in blood cells, serum and expression of the alleles.

At the same time the alleles of different loci can be determined in one test, as a result of which the association with diseases becomes known in a broader context (more loci or gene systems).

The nomenclature for the gene systems can be localised in a simple manner by definitions of polymorphous parts of the loci/genes by using the invention.

The strongly conserved section of the genetic material whose nucleotide sequence is compared, according to the invention, has a greater homology than the polymorphous (less conserved) sections whose sequence is compared in the known methods. The homology at base level, i.e. the percentage of nucleotides which is characteristic of locus or of the allele forms of the genes is at least approximately 50% and preferably at least 58%.

The method according to the invention is especially usable for determining haplotypes of a gene system.

In particular, the method can be used to compare loci of a gene system and alleles of a gene system, such as the gene system of the histocompatibility system. At the same time, it may be a matter of a routine determination of alleles in which a specific typing/identification of the presence of an allele is required (for example, in bone marrow transplants or blood transfusions).

A gene system which is also advantageously suitable for investigation with the method according to the invention is a gene system of one of the members of the immunoglobulin supergene family, in particular the genes of an immunoglobulin (Ig) or the genes of the T-cell receptor (TCR).

The method according to the invention is also suitable for research purposes in which a simpler determination of polymorphous sequences other than those which are characteristic for typing is possible in a gene as a result of selection of other conserved flanking sequences.

The determination of the genotype with the method according to the invention relates, in particular, to tissue typing or cell typing. This can be done, for example, in order to determine the degree of compatibility of transplants. If no, or very few, deviations are found in the polymorphous region between donor and acceptor, a transplant will have a high chance of taking because no rejection takes place on the basis of HLAs foreign to the body. It is also possible to carry out tissue typing or cell typing in order to determine the risk of an HLA-associated disease for an animal. A particular aspect in this connection is the uniform performability and introduction of typing possibilities for, for example, HLA class I alleles which could hitherto be determined only by serological techniques.

Moreover, a gene system of a bacterium, or a virus or of lipo-proteins cna be used a s the gene system whose genetic variation is investigated.

The investigation of the possible variation in the nucleotide sequence of a strongly conserved region with the aid of the method according to the invention can readily be carried out if the strongly conserved section to be investigated is bounded on at least one side, and preferably on both sides, by a completely conserved sequence, i.e. a sequence which is completely identical in all individuals. Said completely conserved sequences have, in particular, a length of at least 5 nucleotides and, particularly preferably, a length of at least 10 nucleotides.

The strongly conserved nucleotide sequences to be investigated can be amplified using the completely conserved sequences. A method which is used with advantage for amplifying the strongly conserved nucleotide sequence is a PCR (polymerase chain reaction) (Saiki R. K., Gelfand D. H., Stoffel S., Scharf S. J., Higuchi R., Horn G. T., Mullis K. B. and Erlich H. A. (1988). Primer directed enzymatic amplification of DNA with a thermostable DNA polymerase, Science 239, 487–491). Other methods of amplifying the sequence to be investigated are also usable in the method according to the invention.

The sequence amplified in this way can then be subjected to direct sequence analysis, to denaturing gradient gel electrophoresis (DGGE) or to temperature-gradient gel electrophoresis (TGGE). The extent to which the denaturing gel system works depends on the discriminating capacity of the gel in relation to the number of different alleles. In other words, the gel system will work well if there is only a limited number of alleles of a locus, such as the lipoprotein alleles, HLA-DQA alleles, HLA-DPB alleles and possibly HLA-DQB alleles, and virus types, and can be used to determine expression of different loci in different cells or tissues.

The amplified DNA or RNA can also be analysed (=typed) by direct sequence determination methods. For routine typing determinations, both analyses may be carried out informatively, reproducibly and in a controlled manner. For gene systems containing several alleles, direct sequence analysis will facilitate the interpretation and therefore the reproducibility by the various centres. The direct sequence analysis method also has advantages for research purposes.

Determination of modifications has hitherto been carried out at DNA level by means of Southern blotting. The different families of TCR and Ig genes can be detected by means of specific amplification and sequencing or DGGE, while the various members of the family can be distinguished by a set of family-specific primers. Another gene system which is directly suitable for this approach is the determination of diverse viruses, for example HPV1-16.

BRIEF DESCRIPTION OF THE DRAWINGS

FIG. 1 shows a nucleotide sequence and polypeptide translation of an HLA DRB allele designated DR1, whose nucleotide and polypeptide sequences are referred to herein as SEQ ID NOS:16–17.

FIGS. 2a and 2b show the nucleotide sequences and polypeptide translations of allele-specific oligonucleotides complementary to several alleles found in members of a human family discussed in Example 2, where FIG. 2a shows oligonucleotide sequences and corresponding polypeptide translations (SEQ ID NOS:18–27) for a first polymorphic region of the DRB allele (upper underlined region of FIG. 1), and FIG. 2b shows oligonucleotide sequences and polypeptide translations (SEQ ID NOS:28–37) for a second polymorphic region (lower underline region of FIG. 1).

FIG. 3a shows nucleotide sequence information (SEQ ID NOS:38–42) obtained with control cell lines in the study described in Example 2 using primers DRB5 and DRB3 (SEQ ID NOS:1–2, respectively), where the sequences shown span polypeptide residues 1–36 of the polypeptide sequence shown in FIG. 1 (see also SEQ ID NO: 17), and where SEQ ID NOS:38–42 correspond to DRB alleles DR1, DR2.1, DR2.5, DRw6.w19 and DRw6.52$^c$, respectively; FIG. 3b shows nucleotide sequence information obtained with samples from the family studied in Example 2, where the sequences designated DR1, DR2.1-like, DR2.5-like, DRw6.w19 and DRw6.52$^c$ correspond to SEQ ID NOS:38, 43, 44, 41 and 42, respectively.

FIG. 4 shows alleles detected by DR1- and DR2 oligos.

DETAILED DESCRIPTION OF THE INVENTION

Selection of Primers

Many alleles of a large number of genes have been sequenced for research purposes. These sequences are stored in the EMBL databank (for Europe) and in the Gene bank (USA), both of which are accessible to subscribers. On the basis of these sequences, the allele-specific oligos (ASO), for example, have been selected from the polymorphous regions and these have then been used to identify different alleles. Most gene systems contain regions of sequences which are not subject to, hardly subject to or very strongly subject to mutations. For the HLA class II gene system, this has been investigated in detail in order to localise the polymorphous regions. References: Gustafason K., Emmoth E., Larhammer D., Bohme J., Hyldig-Nielsen J. J., Peterson P. A. and Rask L. (1984). Mutations and selection in the generation of class II histocompatibility antigen polymorphism. Embo J. 3, 1655–1661; Gustafason K., Wiman K., Larhammer D., Rask L. and Peterson P. A. (1984). Signal sequences distinguish class II histocompatibility antigen beta chains of different loci. Scand. J. Immunol. 19, 91–97.

The presence of usable sequences for the method according to the invention can be detected by more detailed analysis of HLA class I and II sequences which were available from the sequence databanks (EMBL and Genebank), supplemented by self-determined sequences. Primers for class I and other gene systems have been selected from the sequence databank and can be used. Primers based on conserved sequences for the HLA class II loci DRB, DQA, DQB and DPB can be selected on the basis of the sequences already known. Some usable primers are reported in one of the examples below. It is within the scope of the person skilled in the art to select and to test the completely conserved sequences (primers) suitable for the typing he plans.

Applications

To determine lipoprotein polymorphism, the ASO can be radioactively labelled and used as a probe for typing the various alleles which are present in lipoprotein E. Three frequently occurring alleles can also be determined by means of restriction enzyme analysis because, in the case of these three alleles in the polymorphous section, the differences are localised at restriction enzyme sites. All five different alleles can be determined directly by a denaturing gel electrophoresis (Sheffield et al., Identifying DNA polymorphisms by denaturing gradient gelI electrophoreis, in PCR Protocols: A Guide to Methods and Applications, Academic Press Inc., 1990, pages 206–218). There are indications that the different alleles can be detected by direct sequencing since the occurrence of the different alleles is based on differences in nucleotide sequences (McBride et al., Cin. Chem. 35, 2196–2201 (1989)).

In the case of HLA typing, "constant primers" were used to amplify DRB genes of a family in which an abnormal HLA type occurred. After amplification of the DRB genes, cloning in vectors and subsequent sequence analysis, it was found that the "abnormal" HLA type is in fact a new haplotype which cannot be detected by known techniques. In this analysis it was found that the identification of the various alleles can be carried out simply by direct sequencing and localisation of the thymidine nucleotides present in the allele (T-tracking). Automatic sequence determinations have already been carried out for the sequencing of HLA-DQA (McBride et al., 1989, see above). The method followed by them can be used directly with slight modifications for automatic sequence systems to type the alleles of a locus.

After the primers have been selected, "kits" can be assembled for the various gene systems, which kits contain, inter alia, said primers, as a result of which a standardised method is obtained for typing the various alleles. In the first instance, the ApoE and HLA-DRB, DQA DQB and DPB alleles are investigated for general applicability with denaturing gels and by means of sequence analysis.

The invention therefore also relates to a kit for tracing genetic variations in a gene family which contains one or two completely conserved sequences having a length of at least 5 nucleotides as primer(s) and possibly other means for amplifying and analysing a strongly conserved section of the genetic material to be investigated, which section is flanked by the completely conserved nucleotide sequence(s).

EXAMPLES

Example 1

Primers based on conserved sequences have been selected for the HLA class II loci DRB, DQA, DQB and DPB and tested for usability. Shown below are the sequences of some universal primers which have been selected and tested for an amplification reaction (PCR). Two primers are preferably used for each reaction.

DRB5: SEQ ID NO: 1
DRB3: SEQ ID NO: 2
DQA5: SEQ ID NO: 3
DQA3: SEQ ID NO: 4
DQA3.1: SEQ ID NO: 5
DQA3.2: SEQ ID NO: 6
N.B. DQA5 is used in combination with DQA3, DQA3.1 or DQA3.2.
DXA3.2: SEQ ID NO: 7
DXA3: SEQ ID NO: 8
N.B. DXA3 and DXA3.2 are used in combination with DQA.5
DQB5: SEQ ID NO: 9
DQB3: SEQ ID NO: 10
DPB5: SEQ ID NO: 11
DPB3: SEQ ID NO: 12
DPB3SP (alternative for DPB3): SEQ ID NO: 13
APOE.F4: SEQ ID NO: 14
APOE.F6: SEQ ID NO: 15
The combinations DRB5/DRB3, DQA5/DQA3.2 ad DPB5.DPB3SP have been successfully used for sequences.

Example 2

In the family G (two parents, four children) cross reaction was found in the determination for HLA class II alleles having different typing sera by means of the conventional HLA typing method. It was not possible to establish any typing by this means. More detailed analysis by means of restriction fragment length polymorphism (RFLP) and ASO typing resulted in the hypothesis that it was not two alleles of HLA-DRB which occurred in this family in different members of the family, but three, and this had implications for a disease of one of the members of the family to be treated (Tilanus M. G. H., Van Eggermond M. C. J. A., Fei H., Scheuder G. M. Th. and Giphart M. J. (1989). Family with an apparent HLA-DR triplet: Evidence for exchange of functional HLA-DR beta genes between different haplotypes, Exp. Clin. Immunogenetics 6, 162–168). The DNA of this family was studied in more detail in order to be able to establish the genetic basis for this phenomenon. One of the techniques which was used in doing this consisted of sequence analysis of the various alleles of HLA class II loci.

In this family, three DRB alleles have been identified in the DNA of one person, viz. DR1, DR2 and DRw6, on the basis of positive identification with allele-specific oligos (triplet). The allele-specific oligos detect the corresponding sequences for the regions which also differ at protein level. FIG. 1 shows the nucleotide sequence of DR1 with the derived amino acid sequence in three-letter and one-letter code. The underlined regions indicate the location of allele-specific oligos. The nucleotide sequence and the associated amino acid sequence of the allele-specific oligonucleotides of the other alleles present in this family are shown in FIGS. 2a and 2b. FIG. 2a shows the nucleotide variation in a first polymorphous region and FIG. 2b that in a second polymorphous region, corresponding to the underlined regions in FIG. 1. For a more detailed analysis of the DRB genes, the universal primers DRB5S and DRB3E described were used. In a control study, the use of the universal primers for identification of the DRB alleles DR1, DR2 and DRw6 was tested, but no deviations were found in these sequences. The results of the sequence analysis of control cell lines and DNA of family G are shown in FIGS. 3a and 3b, respectively, in the form of the amino acid sequence using the one-letter code.

It is evident from this that there is a recombined haplotype in this family, DR1 and DR2 alleles being involved. The DRw6.w19 and DRw6.52$^c$ alleles are identical to the control sequences. It appears that the alleles which are detected by the DR1- specific oligos and by the DR2-specific oligo occur next to teach other (FIG. 4). There is therefore no question of three alleles being present here but of a DRB haplotype not previously identified. In another section of the gene, a specific sequence has been identified for this DR1+2 haplotype.

Of other loci (DQB, DQA and DPB) in this family, it has now been established by using universal primers that there are also only two (unmutated) alleles. In addition, said haplotype can be characterised by the presence of conserved specific sequences.

---

I claim:

1. A method of determining a genotype of a selected HLA locus of a human subject, comprising
  obtaining a nucleic acid sample from the subject, where said sample contains both parental alleles of an HLA locus, and the HLA locus is selected from the group consisting of HLA-A, HLA-B, HLA-C, HLA-DP, HLA-DQ, and HLA-DR,
  amplifying a polymorphic region within said locus by polymerase chain amplification reactions using first and second primers that are complementary to first and second nucleotide regions in the selected locus, where said first and second regions (i) flank the polymorphic region, and (ii) are conserved completely among alleles of the locus, and
  co-sequencing both parental alleles of the amplified polymorphic region via a primer-extension reaction using at least one of said first and second primers as initiating primer, without separating the parental alleles, to determine the subject's genotype for the selected locus, whereby said genotype is determined without independently sequencing either allele alone.

2. The method of claim 1, wherein said primers are at least 10 nucleotides in length.

3. The method of claim 1, wherein the first or second primer has the sequence depicted in SEQ. ID NO:1.

4. The method of claim 1, wherein the first or second primer has the sequence depicted in SEQ. ID NO:2.

5. The method of claim 1, wherein the first or second primer has the sequence depicted in SEQ. ID NO:3.

6. The method of claim 1, wherein the first or second primer has the sequence depicted in SEQ. ID NO:4.

7. The method of claim 1, wherein the first or second primer has the sequence depicted in SEQ. ID NO:5.

8. The method of claim 1, wherein the first or second primer has the sequence depicted in SEQ. ID NO:6.

9. The method of claim 1, wherein the first or second primer has the sequence depicted in SEQ. ID NO:7.

10. The method of claim 1, wherein the first or second primer has the sequence depicted in SEQ. ID NO:8.

11. The method of claim 1, wherein the first or second primer has the sequence depicted in SEQ. ID NO:9.

12. The method of claim 1, wherein the first or second primer has the sequence depicted in SEQ. ID NO:10.

13. The method of claim 1, wherein the first or second primer has the sequence depicted in SEQ. ID NO:11.

14. The method of claim 1, wherein the first or second primer has the sequence depicted in SEQ. ID NO:12.

15. The method of claim 1, wherein the first or second primer has the sequence depicted in SEQ. ID NO:13.

16. The method of claim 1, wherein the first or second primer has the sequence depicted in SEQ. ID NO:14.

17. The method of claim 1, wherein the first or second primer has the sequence depicted in SEQ. ID NO:15.

* * * * *